United States Patent [19]

Dalby et al.

[11] Patent Number: 5,202,110
[45] Date of Patent: Apr. 13, 1993

[54] FORMULATIONS FOR DELIVERY OF BECLOMETHASONE DIPROPRIONATE BY METERED DOSE INHALERS CONTAINING NO CHLOROFLUOROCARBON PROPELLANTS

[75] Inventors: Richard N. Dalby; Peter R. Byron, both of Richmond, Va.

[73] Assignee: Virginia Commonwealth University, Richmond, Va.

[21] Appl. No.: 824,030

[22] Filed: Jan. 22, 1992

[51] Int. Cl.$^5$ ................................................ A61L 9/04
[52] U.S. Cl. ...................................... 424/45; 424/43; 252/305
[58] Field of Search ...................... 424/45, 43; 252/305

[56] References Cited

U.S. PATENT DOCUMENTS 4,810,488  3/1989  Jinks ..................................... 424/45

FOREIGN PATENT DOCUMENTS 0372777  6/1990  European Pat. Off. .
994734  6/1965  United Kingdom .

Primary Examiner—Richard L. Raymond
Assistant Examiner—Shailendra Kumar
Attorney, Agent, or Firm—Whitham & Marhoefer

[57] ABSTRACT

Beclomethasone diproprionate (BDP) forms a clathrate with HCFC-123, dimethyl ether (DME) and HCFC-141b which are less harmful propellants than the CFC propellants currently used in metered dose inhalers (MDIs). The clathrate can be remicronized and suspended for use in an MDI. BDP also is completely dissolved by DME based propellant blends and certain HCFC 123 propellant blends. Using propellant blends which completely dissolve BDP will assure more efficient dosing with an MDI.

21 Claims, 22 Drawing Sheets

| High Vapor Pressure Component | | | Low Vapor Pressure Component | | |
|---|---|---|---|---|---|
| Name | Weight % of Blend | | Name | Weight % of Blend | |
| | Target | Actual | | Target | Actual |
| HFC-134a | 55.9 | 58.1 | HC-31 | 44.1 | 41.9 |
| HFC-134a | 67.9 | 67.8 | HC-17 | 32.1 | 32.2 |
| HFC-134a | 57.7 | 57.7 | CFC-11 | 42.3 | 42.3 |
| HFC-134a | 56.1 | 56.1 | HCFC-123 | 43.9 | 43.9 |
| HFC-134a | 44.7 | 44.1 | CFC-114 | 55.3 | 55.9 |
| HFC-134a | 39.8 | 39.7 | PP50 | 60.2 | 60.3 |
| HFC-134a | 62.3 | 62.1 | HCFC-141b | 37.7 | 37.9 |
| HFC-134a | 100.0 | 100.0 | NONE | 0.0 | 0.0 |
| CFC-12 | 70.5 | 70.6 | HC-31 | 29.5 | 29.4 |
| CFC-12 | 79.9 | 80.0 | HC-17 | 20.1 | 20.0 |
| CFC-12 | 72.0 | 72.1 | CFC-11 | 28.0 | 27.9 |
| CFC-12 | 70.7 | 70.6 | HCFC-123 | 29.3 | 29.4 |
| CFC-12 | 60.4 | 60.4 | CFC-114 | 39.6 | 39.6 |
| CFC-12 | 55.5 | 55.4 | PP50 | 44.5 | 44.6 |
| CFC-12 | 75.7 | 75.7 | HCFC-141b | 24.3 | 24.3 |
| HC-108 | 22.1 | 22.2 | HC-31 | 77.9 | 77.8 |
| HC-108 | 32.1 | 31.9 | HC-17 | 67.9 | 68.1 |
| HC-108 | 23.4 | 23.3 | CFC-11 | 76.6 | 76.7 |
| HC-108 | 22.3 | 22.3 | HCFC-123 | 77.7 | 77.7 |
| HC-108 | 15.3 | 15.3 | CFC-114 | 84.7 | 84.7 |
| HC-108 | 12.9 | 12.9 | PP50 | 87.1 | 87.1 |
| HC-108 | 27.0 | 26.9 | HCFC-141b | 73.0 | 73.1 |
| DME | 60.0 | 60.0 | HC-31 | 40.0 | 40.0 |
| DME | 71.5 | 71.5 | HC-17 | 28.5 | 28.5 |
| DME | 61.8 | 61.7 | CFC-11 | 38.2 | 38.3 |
| DME | 60.3 | 60.4 | HCFC-123 | 39.7 | 39.6 |
| DME | 49.0 | 48.9 | CFC-114 | 51.0 | 51.1 |
| DME | 43.9 | 43.8 | PP50 | 56.1 | 56.2 |
| DME | 66.2 | 66.3 | HCFC-141b | 33.8 | 33.7 |

FIGURE 1

| FORMULATION | VAPOR PRESSURE (psia) @25°C | | >10 psi difference between calculated and measured V.P. |
|---|---|---|---|
| | CALCULATED | MEASURED | |
| HFC-134a / HC-31 | 67 | 90 | yes |
| HFC-134a / HC-17 | 67 | 85 | yes |
| HFC-134a / CFC-11 | 68 | 70 | no |
| HFC-134a / HCFC-123 | 68 | 65 | no |
| HFC-134a / CFC-114 | 68 | 70 | no |
| HFC-134a / PP50 | 67 | 73 | no |
| HFC-134a / HCFC-141b | 67 | 70 | no |
| HFC-134a | 96 | 90 (20C) | no |
| CFC-12 / HC-31 | 72 | 65 | no |
| CFC-12 / HC-17 | 73 | 65 | no |
| CFC-12 / CFC-11 | 74 | 65 | no |
| CFC-12 / HCFC-123 | 75 | 65 | no |
| CFC-12 / CFC-114 | 65 | 62 | no |
| CFC-12 / PP50 | 74 | 68 | no |
| CFC-12 / HCFC-141b | 74 | 70 | no |
| HC-108 / HC-31 | 67 | 60 | no |
| HC-108 / HC-17 | 67 | 60 | no |
| HC-108 / CFC-11 | 69 | 70 | no |
| HC-108 / HCFC-123 | 70 | 73 | no |
| HC-108 / CFC-114 | 70 | 68 | no |
| HC-108 / PP50 | 69 | 90 | yes |
| HC-108 / HCFC-141b | 68 | 75 | no |
| DME / HC-31 | 67 | 65 (20C) | no |
| DME / HC-17 | 67 | 65 | no |
| DME / CFC-11 | 67 | 65 | no |
| DME / HCFC-123 | 67 | 65 | no |
| DME / CFC-114 | 68 | 65 | no |
| DME / PP50 | 67 | 70 | no |
| DME / HCFC-141b | 67 | 65 | no |

FIGURE 2

| FORMULATION | CALCULATED DENSITY (g/ml, 25°C) | MEASURED DENSITY (g/ml, 25°C) |
|---|---|---|
| HFC-134a / HC-31 | 0.930 | 0.764 |
| HFC-134a / HC-17 | 1.02 | 0.861 |
| HFC-134a / CFC-11 | 1.33 | 1.306 |
| HFC-134a / HCFC-123 | 1.33 | 1.324 |
| HFC-134a / CFC-114 | 1.36 | 1.330 |
| HFC-134a / PP50 | 1.45 | 1.407 |
| HFC-134a / HCFC-141b | 1.23 | 1.223 |
| HFC-134a | 1.22 | 1.220 |
| CFC-12 / HC-31 | 1.109 | 0.932 |
| CFC-12 / HC-17 | 1.176 | 1.040 |
| CFC-12 / CFC-11 | 1.369 | 1.376 |
| CFC-12 / HCFC-123 | 1.364 | 1.372 |
| CFC-12 / CFC-114 | 1.381 | 1.380 |
| CFC-12 / PP50 | 1.442 | 1.420 |
| CFC-12 / HCFC-141b | 1.302 | 1.311 |
| HC-108 / HC-31 | 0.55 | 0.543 |
| HC-108 / HC-17 | 0.56 | 0.553 |
| HC-108 / CFC-11 | 1.26 | 1.030 |
| HC-108 / HCFC-123 | 1.25 | 1.036 |
| HC-108 / CFC-114 | 1.32 | 1.127 |
| HC-108 / PP50 | 1.46 | 1.212 |
| HC-108 / HCFC-141b | 1.04 | 0.900 |
| DME / HC-31 | 0.62 | 0.611 |
| DME / HC-17 | 0.64 | 0.632 |
| DME / CFC-11 | 0.98 | 0.849 |
| DME / HCFC-123 | 0.98 | 0.856 |
| DME / CFC-114 | 1.07 | 0.915 |
| DME / PP50 | 1.19 | 0.954 |
| DME / HCFC-141b | 0.85 | 0.797 |

FIGURE 3

| FORMULATION | SOLUBILITY AT 25 C (ug/g) | |
|---|---|---|
| | INITIAL | 8 WEEKS |
| CFC-12 / HC-31 | 51.86 | 59.92 |
| CFC-12 / HC-17 | 53.04 | 63.72 |
| CFC-12 / CFC-11 | 58.63 | 69.09 |
| CFC-12 / HCFC-123 | 565.96 | 594.01 |
| CFC-12 / CFC-114 | 31.19 | 69.60 |
| CFC-12 / PP50 | 28.86 | 35.75 |
| CFC-12 / HCFC-141b | 111.73 | 104.68 |
| HFC-134a / HC-31 | 189.97 | 175.93 |
| HFC-134a / HC-17 | 361.75 | 230.30 |
| HFC-134a / CFC-11 | 721.17 | 338.05 |
| HFC-134a / HCFC-123 | 2090.13 | 1049.74 |
| HFC-134a / CFC-114 | 113.03 | 107.99 |
| HFC-134a / HCFC-141b | 675.58 | 501.30 |
| HFC-134a | 98.77 | 139.34 |
| DME / HC-31 | 2009.59 | 1810.69 |
| DME / HC-17 | 4336.24 | 3988.59 |
| DME / CFC-11 | 7285.51 | 6412.00 |
| DME / HCFC-123 | 6856.24 | 6126.41 |
| DME / CFC-114 | 2411.94 | 1954.96 |
| DME / HCFC-141b | >10425.03 | >10425.03 |
| HC-108 / HC-31 | 150.56 | 166.04 |
| HC-108 / HC-17 | 249.62 | 241.50 |
| HC-108 / CFC-11 | 139.57 | 102.89 |
| HC-108 / HCFC-123 | 5128.12 | 4715.89 |
| HC-108 / CFC-114 | 67.18 | 81.71 |
| HC-108 / HCFC-141b | 467.61 | 352.09 |

FIGURE 4

| FORMULATION | INITIAL PHISICAL CHARACTERIZATION | | |
|---|---|---|---|
| | BECLOMETHASONE | OLEIC ACID | PROPELLANT |
| HFC-134a / HC-31 | sinks, aggregated | dissolved | 1 phase |
| HFC-134a / HC-17 | sinks, aggregated | dissolved | 1 phase |
| HFC-134a / CFC=11 | sinks, aggregated some stuck to glass | dissolved | 1 phase |
| HFC-134a / HCFC-123 | dissolved | dissolved | 1 phase |
| HFC-134a / CFC-114 | floats, aggregated | dissolved | 1 phase |
| HFC-134a / PP50 | floats, aggregated some stuck to glass | undissolved | 1 phase |
| HFC-134a / HCFC-141b | sinks, some crystals | dissolved | 1 phase |
| HFC-134a | sinks, aggregated | undissolved | 1 phase |
| CFC-12 / HC-31 | sinks, aggregated | dissolved | 1 phase |
| CFC-12 / HC-17 | sinks, aggregated | dissolved | 1 phase |
| CFC-12 / CFC-11 | sinks, not aggregated | dissolved | 1 phase |
| CFC-12 / HCFC-123 | dissolved initially, later crystallized | dissolved | 1 phase |
| CFC-12 / CFC-114 | floats, aggregated | undissolved | 1 phase |
| CFC-12 / PP50 | floats, aggregated | undissolved | 1 phase |
| CFC-12 / HCFC-141b | sinks, some crystals | dissolved | 1 phase |

FIGURE 5a

| FORMULATION | INITIAL PHISICAL CHARACTERIZATION | | |
|---|---|---|---|
| | BECLOMETHASONE | OLEIC ACID | PROPELLANT |
| HC-108 / HC-31 | sinks, aggregated, some stuck to glass | undissolved | 1 phase |
| HC-108 / HC-17 | sinks, aggregated some stuck to glass | partially dissolved | 1 phase |
| HC-108 / CFC-11 | sinks, aggregated, crystals | undissolved | 1 phase |
| HC-108 / HCFC-123 | dissolved | dissolved | 1 phase |
| HC-108 / CFC-114 | sinks, aggregated, crystals | undissolved | 1 phase |
| HC-108 / PP50 | sinks, aggregated, some stuck to glass | partially dissolved | 1 phase |
| HC-108 / HCFC-141b | sinks, some crystals | dissolved | 1 phase |
| DME / HC-31 | dissolved | dissolved | 1 phase |
| DME / HC-17 | dissolved | dissolved | 1 phase |
| DME / CFC-11 | dissolved | dissolved | 1 phase |
| DME / HCFC-123 | dissolved | dissolved | 1 phase |
| DME / CFC-114 | dissolved, black particles | dissolved | 1 phase |
| DME / PP50 | sinks, crystals | dissolved | 1 phase |
| DME / HCFC-141b | dissolved | dissolved | 1 phase |

FIGURE 5b

| FORMULATION | INITIAL PHISICAL CHARACTERIZATION AFTER 3 MONTHS | | |
|---|---|---|---|
| | BECLOMETHASONE | OLEIC ACID | PROPELLANT |
| HFC-134a / HC-31 | sinks, crystals, some stuck to glass | dissolved | 1 phase |
| HFC-134a / HC-17 | sinks, crystals, some stuck to glass | dissolved | 1 phase |
| HFC-134a / CFC-11 | sinks, crystals, some stuck to glass | dissolved | 1 phase |
| HFC-134a / HCFC-123 | floats, some crystals, mostly dissolved | dissolved | 1 phase |
| HFC-134a / CFC-114 | sinks, crystals, some stuck to glass | dissolved | 1 phase |
| HFC-134a / PP50 | floats, crystals, some stuck to glass | undissolved | 1 phase |
| HFC-134a / HCFC-141b | sinks, crystals, some stuck to glass, some dissolved | dissolved | 1 phase |
| HFC-134a | sinks, crystals, some stuck to glass, some dissolved | dissolved | 1 phase |
| CFC-12 / HC-31 | sinks, crystals, some stuck to glass | dissolved | 1 phase |
| CFC-12 / HC-17 | sinks, crystals, some stuck to glass | dissolved | 1 phase |
| CFC-12 / CFC-11 | sinks, crystals, some stuck to glass | dissolved | 1 phase |

FIGURE 5c

| FORMULATION | INITIAL PHISICAL CHARACTERIZATION AFTER 3 MONTHS | | |
|---|---|---|---|
| | BECLOMETHASONE | OLEIC ACID | PROPELLANT |
| CFC-12 / HCFC-123 | crystalline, some stuck to glass | dissolved | 1 phase |
| CFC-12 / CFC-114 | floats, crystals, some stuck to glass | undissolved | 1 phase |
| CFC-12 / PP50 | floats, aggregated some stuck to glass | undissolved | 1 phase |
| CFC-12 / HCFC-141b | sinks, crystals, some stuck to glass | dissolved | 1 phase |
| HC-108 / HC-31 | sinks, crystals, some stuck to glass, ring around bottle | dissolved | 1 phase |
| HC-108 / HC-17 | sinks, crystals, some stuck to glass | dissolved | 1 phase |
| HC-108 / CFC-11 | sinks, crystals, some stuck to glass | dissolved | 1 phase |
| HC-108 / HCFC-123 | dissolved | dissolved | 1 phase |
| HC-108 / CFC-114 | sinks, aggregated, crystals, some stuck to glass, ring around bottle | undissolved | 1 phase |
| HC-108 / PP50 | sinks, aggregated, crystals, some stuck to glass, ring around bottle | undissolved | 1 phase |
| HC-108 / HCFC-141b | sinks, crystals, some stuck to glass | dissolved | 1 phase |
| DME / HC-31 | dissolved | dissolved | 1 phase |
| DME / HC-17 | dissolved | dissolved | 1 phase |
| DME / CFC-11 | dissolved | dissolved | 1 phase |
| DME / HCFC-123 | dissolved, few black particles | dissolved | 1 phase |
| DME / CFC-114 | dissolved, few black particles | dissolved | 1 phase |
| DME / PP50 | sinks, crystals | dissolved | 1 phase |
| DME / HCFC-141b | dissolved | dissolved | 1 phase |

FIGURE 5d

| FORMULATION | APPROXIMATE FLAME EXTENSION (cm) | OBSERVATIONS |
|---|---|---|
| HFC-134a / HC-31 | 25 | blue flame with orange tip, retreats to mouthpiece |
| HFC-134a / HC-17 | 30 | blue flame with orange tip, retreats to mouthpiece |
| HFC-134a / CFC-11 | 0 | no effect on flame |
| HFC-134a / HCFC-123 | 0 | orange sparks in flame |
| HFC-134a / CFC-114 | 0 | orange sparks in flame |
| HFC-134a / PP50 | 0 | orange sparks in flame |
| HFC-134a / HCFC-141b | 0 | orange sparks in flame |
| HFC-134a | 0 | no effect on flame |
| CFC-12 / HC-31 | 20 | green/blue flame, slightly orange tip |
| CFC-12 / HC-17 | 20 | green/blue flame, slightly orange tip |
| CFC-12 / CFC-11 | 0 | no effect on flame |
| CFC-12 / HCFC-123 | 0 | no effect on flame |
| CFC-12 / CFC-114 | 0 | orange sparks in flame |
| CFC-12 / PP50 | 0 | orange sparks in flame |
| CFC-12 / HCFC-141b | 0 | orange sparks in flame |

FIGURE 7a

| FORMULATION | APPROXIMATE FLAME EXTENSION (cm) | OBSERVATIONS |
|---|---|---|
| HC-108 / HC-31 | 40 | blue flame with orange tip, retreats to mouthpiece |
| HC-108 / HC-17 | 45 | blue flame with orange tip, retreats to mouthpiece |
| HC-108 / CFC-11 | 25 | blue/green flame with orange tip |
| HC-108 / HCFC-123 | 20 | blue/green flame with orange tip |
| HC-108 / CFC-114 | 15 | blue/green flame with orange tip |
| HC-108 / PP50 | 15 | blue flame |
| HC-108 / HCFC-141b | 30 | blue/green flame with orange tip |
| DME / HC-31 | 40 | blue flame with orange tip, retreats to mouthpiece |
| DME / HC-17 | 40 | blue flame with orange tip, retreats to mouthpiece |
| DME / CFC-11 | 30 | blue flame, orange tip |
| DME / HCFC-123 | 35 | blue flame, orange tip |
| DME / CFC-114 | 30 | blue flame, orange tip |
| DME / PP50 | 30 | blue flame, pink tip |
| DME / HCFC-141b | 30 | blue flame, orange tip |

FIGURE 7b

| FORMULATION | EXPECTED SHOT WT. (mg, 25°C) | ACTUAL MEAN SHOT WT. (mg) | |
|---|---|---|---|
| | | INITIAL | 3 MONTHS |
| HFC-134a / HC-31 | 48 | 50 | 43 |
| HFC-134a / HC-17 | 54 | 56 | 49 |
| HFC-134a / CFC-11 | 82 | 81 | 81 |
| HFC-134a / HCFC-123 | 83 | 80 | 74 |
| HFC-134a / CFC-114 | 84 | 81 | 73 |
| HFC-134a / PP50 | 89 | 87 | 83 |
| HFC-134a / HCFC-141b | 77 | 72 | 73 |
| HFC-134a | 77 | 82 | 79 |
| CFC-12 / HC-31 | 59 | 61 | 56 |
| CFC-12 / HC-17 | 66 | 66 | 63 |
| CFC-12 / CFC-11 | 87 | 85 | 80 |
| CFC-12 / HCFC-123 | 86 | 83 | 80 |
| CFC-12 / CFC-114 | 87 | 91 | 87 |
| CFC-12 / PP50 | 89 | 89 | 86 |
| CFC-12 / HCFC-141b | 83 | 78 | 77 |
| HC-108 / HC-31 | 34 | 36 | 34 |
| HC-108 / HC-17 | 35 | 35 | 34 |
| HC-108 / CFC-11 | 65 | 62 | 58 |
| HC-108 / HCFC-123 | 65 | 96 | 46 |
| HC-108 / CFC-114 | 71 | 70 | 71 |
| HC-108 / PP50 | 76 | 71 | 70 |
| HC-108 / HCFC-141b | 57 | 49 | 48 |
| DME / HC-31 | 38 | 37 | 41 |
| DME / HC-17 | 40 | 38 | 42 |
| DME / CFC-11 | 53 | 46 | 56 |
| DME / HCFC-123 | 54 | 43 | 50 |
| DME / CFC-114 | 58 | 55 | 60 |
| DME / PP50 | 60 | 56 | 64 |
| DME / HCFC-141b | 50 | 44 | 48 |

FIGURE 8

FORMULATIONS FOR DELIVERY OF BECLOMETHASONE DIPROPRIONATE BY METERED DOSE INHALERS CONTAINING NO CHLOROFLUOROCARBON PROPELLANTS

BACKGROUND OF THE INVENTION

1. Field of the Invention

The present invention generally relates to formulations for use in Metered Dose Inhalers and, more particularly, to improved formulations with reduced ozone-depletion and global warming potentials.

2. Description of the Prior Art

Metered-dose inhalers (MDIs) are a well-known form of treatment for numerous respiratory conditions. MDIs comprise a pressure resistant container fitted with a metering valve. The container is filled with a medicament, such as a bronchodilator or corticosteroid, which is dissolved or suspended in a liquified propellant. Actuation of the metering valve allows a small portion of the spray product to be released, whereby the pressure of the liquified propellant carries the drug particles out of the container to the patient. The valve actuator is used to direct the aerosol spray into the patient's mouth.

Typically the liquefied propellants comprise 70–99 wt % of the formulation and, heretofore, have generally been chlorofluorocarbons (CFCs) or blends of two or more CFCs, such as trichlorofluoromethane ($CCl_3F$ or CFC-11), dichlorodifluoromethane ($CCl_2F_2$ or CFC-12, and 1,2-dichloro-1,1,2,2-tetrafluoroethane ($CClF_2$—$CClF_2$ or CFC-114). CFC propellants are ideal for use in MDIs because they exhibit low toxicity, chemical stability and high purity. Recently, however, the use of CFCs has come under sharp attack because their high resistance to degradation, which is a desirable property in MDI formulations, also allows CFCs to persist in the atmosphere and thereby cause considerable ozone-depletion and global-warming. Signatory countries to the *Montreal Protocol on Substances That Deplete the Ozone Layer* have now begun to implement the agreed-upon control measures on CFCs which require progressively decreasing production of CFCs culminating in their complete ban by the year 2,000 a.d.

Hydrochlorofluorocarbons (HCFCs), hydrofluorocarbons (HFCs), hydrocarbons (HCs) and other propellants such as dimethylether (DME) are now being considered as replacements for CFCs. CFCs are alkyl molecules with chloro and fluoro moieties on the carbon backbone. HCFCs differ from CFCs in that they contain one or more hydrogen atoms per molecule, which makes them less chemically stable than CFCs. HCFCs often have low vapor pressures at ambient temperature, which is not desirable in MDIs. However, their ozone-depletion and global-warming potentials are significantly lower than those of CFCs. HFCs contain no chlorine and, therefore, have no ozone-depletion potential. They are generally nonflammable, but are poorer solvents than HCFCs or CFCs. The global-warming potential of HFCs is similar to that of HCFCs. HCs lack toxicity, are low in cost, and have an infinitely variable vapor pressure between 31 and 125 psia. Their major disadvantages are considered to be their flammability and low liquid density.

There are two types of formulations administered using MDIs: solutions and suspensions. In conventional solution-type MDIs, a drug is dissolved with the aid of non-volatile cosolvents such as ethanol. In suspension formulations, small micronized particles of undissolved drug are distributed in the propellant blend. A common suspension formulation which is administered to asthmatics contains the drug beclomethasone diproprionate (BDP). When BDP is dissolved in a mixture of CFCs containing CFC-11, rapid crystal growth occurs. This has been attributed to an association between BDP and CFC-11 known as a "clathrate". If large crystals are permitted to form in an MDI, then, upon inhalation, the particles will impact the oropharynx rather than the bronchioles or pulmonary regions of the lung where they are required to exert their therapeutic effects. Large particles may also disrupt the operation of the metering valve. These problems have been overcome in some prior art CFC formulations by using a method of preswelling BDP particles by exposure to CFC-11 to form the clathrate, then remicronizing to produce small particles which are mixed with the other aerosol formulation ingredients.

SUMMARY OF THE INVENTION

It is therefore an object of the present invention to provide alternative MDI formulations containing BDP and non-CFC propellants which are more environmentally acceptable then CFC-based formulations.

According to the invention, experiments were conducted to reformulate a typical MDI product to reduce or eliminate the use of CFCs. In the experiments, BDP was used as the drug product and oleic acid was used as the surfactant. The ideal alternative propellants will satisfy the following criteria: (1) the propellant or propellant blend should consist of a single liquid phase at room temperature, (2) the surfactant (e.g., oleic acid) should dissolve in the propellant or propellant blend, (3) the micronized drug (e.g., BDP) should be easily dispersible in the propellant or propellant blend with the aid of the surfactant, or completely dissolve, (4) the vapor pressure should range between 50–110 psia at 25° C., (5) the formulation may contain a low vapor pressure component to facilitate slurry preparation which is typically used for packaging MDI products, (6) the aerosolized drug particle size following spraying should be as small as possible to maximize penetration into the lung (e.g. 0.1–10 μm), and (7) the propellant should be compatible with existing manufacturing equipment.

The types of propellants examined included CFCs (CFC-11, CFC-12, and CFC-114), HCFCs (1,1-dichloro-1-fluoroethane ($CCl_2F$—$CH_3$ or HCFC-141b), and 1,1-dichloro-2,2,2-trifluoroethane ($CCl_2H$—$CF_3$ or HCFC-123)), HFCs (1,1,1,2-tetrafluoroethane ($CF_3$—$CH_2F$ or HFC-134a)), HCs (n-butane ($C_4H_{10}$ or HC-17), iso-butane ($C_4H_{10}$ or HC-31), and propane ($C_3H_8$ or HC-108)), perfluoropentane ($_5F_{12}$ or PP-50) and dimethylether ($CH_3$—O—$CH_3$ or DME). The CFC, HCFC, HFC and DME propellants are commercially available from the E.I. DuPont De Nemours Company of Delaware. The HC propellants are commercially available from Phillips 66 Chemical Company of Oklahoma. PP-50 is available from RTZ Chemicals of Bristol, U.K. In the experiments, two-component propellant blends and HFC-134a alone were evaluated in the presence of micronized BDP and oleic acid. The results of the experiments reported herein include vapor pressure (which ranged between 65–90 psia at 25° C.), BDP dispersion characteristics, oleic acid solubility, number of liquid phases, density (which ranged between 0.55–1.46 g/ml at 25° C.), flame extension (which varied from 45 cm to non-flammable), and differential scanning calorimetry (DSC) thermograms.

BRIEF DESCRIPTION OF THE DRAWINGS

The foregoing and other objects, aspects and advantages will be better understood from the following detailed description of a preferred embodiment of the invention with reference to the drawings, in which:

FIG. 1 is a table showing the weight of propellants used in several test formulations, these formulations also being referred to in FIGS. 2-5 and 7-8;

FIG. 2 is table showing the calculated and measured vapor pressures of several test formulations;

FIG. 3 is a table showing the calculated and measured density of several propellant blend combinations;

FIG. 4 is a table showing the solubility of BDP in several test formulations;

FIG. 5a-b are a tables showing the visual characterization of the BDP and oleic acid components in several test formulations initially;

FIGS. 5c-d are tables showing the visual characterization of the BDP and oleic acid components of the test formulations of FIG. 5a after three months time;

FIG. 7a-b are tables showing the observed flame extension for several test formulations sprayed towards an open flame; and FIG. 8 is a table showing average shot weight per actuation initially and after three months for several test formulations.

DETAILED DESCRIPTION OF A PREFERRED EMBODIMENT OF THE INVENTION

Various experiments have been performed with several different test formulations in order to determine acceptable propellant systems which might be utilized in the delivery of BDP via MDIs to patients suffering from respiratory disorders. The primary focus of the experiments was to determine suitable alternatives to the CFC propellants that are presently in widespread use. Some of the properties which were considered were physical properties (e.g. vapor pressure, boiling point, density, heat of vaporization and molar volume), flammability in end-use, compatibility with existing packaging components and manufacturing plants, and availability at a reasonable cost.

Referring now to the drawings, and more particularly to FIG. 1, several different test formulations containing high and low vapor pressure propellant components, with the exception of the test formulation containing HFC-134a as the sole propellant, were prepared. Each formulation contained 3.2 mg oleic acid and 31.7 mg BDP. Each formulation was designed to have 40 ml of liquified propellant and was intended to yield a metered dose equivalent to Beclovent®, which is a CFC-12/CFC-11 propellant blend with BDP that is currently used in several commercial MDI formulations.

The vapor pressure of all propellant blends was calculated with the assumption that all propellants behaved as ideal liquids which obey Raoult's law. Using actual propellant blend density at 25° C., the formulations were calculated to contain BDP at a concentration of 50 μg/63 μl. The formulations were prepared by adding the oleic acid and BDP to pressure resistant aerosol containers, which are commercially available from the Wheaton Glass Company of Mays Landing, N.J., then fitting the containers with either continuous or metering valves from the Bespak Company of Cary, N.C., using commercially available Pamasol small scale aerosol packaging equipment available from Pfaffikon of Switzerland. Excess low pressure propellant was added through the valve, and the vapor vented to the correct weight. The low pressure component present in each of the test formulations presented in FIG. 1, except for the formulation containing HFC-134a alone (hence, no low pressure component), should facilitate slurry formation during commercial manufacturing processes, such as cold or pressure filling. High pressure propellant, defined as a propellant having vapor pressure exceeding 66 psia at 25° C., was then added through the valve to the correct weight. The formulations were shaken and ultrasonicated for the purpose of suspending or dissolving the BDP and dissolving the oleic acid. FIG. 1 provides both the target and the actual weight percentages achieved in the test formulations.

FIG. 2 is a table showing the calculated and measured vapor pressures of the test formulations at 25° C. The vapor pressure and density reported by the supplier of each propellant was used as the basis for all calculations, and the vapor pressures were calculated assuming ideal behavior based on the actual composition of the propellant blends in FIG. 1. The actual vapor pressures were measured using an unpurged gauge and determined to the nearest 5 psi. Many of the propellant blends investigated yielded vapor pressures close to the target value of 66 psia at 25° C. Hence, FIG. 2 demonstrates that it is possible to achieve vapor pressures similar to those encountered in current CFC-based MDI formulations using alternative propellants. In most cases, the measured pressure exceeded the calculated, which is indicative of a positive deviation from Raoult's law and probably indicative of reduced intermolecular bonding between dissimilar propellant molecules.

FIG. 3 is a table showing the calculated and measured densities of the propellant blends used in combination with BDP. The blends contained the same propellants as the formulations shown in FIG. 1, but contained no oleic acid or BDP. The calculated density at 25° C. was determined assuming ideal mixing. Density was measured using a Parr vibrating U-tube densitometer modified to accept volatile propellants. While dramatic density differences between drug and propellant blend are not dispositive of the utility of a propellant blend, mismatches can result in poor suspension stability. For example, if BDP floats to the propellant surface due to a mismatch in density, a lower than expected dose is likely to be released during the first actuation following a period of quiescence. The largest density difference between drug and propellant occurred in the pure HC based formulation. The excellent dispersibility of the BDP particles appeared to compensate for the density difference resulting in a relatively stable suspension.

FIG. 4 is a table showing the measured solubility in μg/g of various formulations at a temperature of 25° C. both initially and after eight weeks of storage. The aim of MDI's is to deliver the maximum amount of drug to the respiratory tract and minimize deposition in the oropharynx. In order to achieve this goal, stable aerosol particles having small aerodynamic diameters are required. Sprayed suspended solids are known to produce droplets and particles, with median aerodynamic sizes greater than solutions. Thus, a propellant blend in which BDP is highly soluble implies that more drug will reach the target area of the lung. Moreover, erratic dosing can be minimized and crystal growth problems do not occur. FIGS. 3 and 4 show that in some propellant formulations, it was possible to dissolve BDP completely at a concentration of 50 μg/63 μl, an observation confirmed in FIGS. 5a and 5b. These formulations included DME blended with HC-31, HC-17, HCFC-123 or HCFC-141b, HC-108 blended with HCFC-123, and HFC-134a blended with HCFC-123.

FIGS. 5a–d show the results of a visual examination of each of the formulations initially (FIG. 5a–b) and after three months (FIGS. 5c–d). The formulations containing either DME blended with HC-31, HC-17, HCFC-123 or HCFC-141b, HC-108 blended with HCFC-123, or HFC-134a blended with HCFC-123 remained in a stable solution form after three months. In most of the test formulations, oleic acid dissolved completely at ambient temperature. All propellant blends investigated displayed a single liquid phase at room temperature, which is an important characteristic of propellant systems for use in MDIs.

While complete solubility of BDP in the propellant formulation is most desirable, complete dissolution is difficult to achieve without the use of nonvolatile co-solvents. Furthermore, formulations showing intermediate BDP solubility in the propellant or propellant blends may exhibit undesirable characteristics, such as crystal growth. Propellant blends in which BDP is negligibly soluble, or present as a remicronized clathrate may be formulated as a suspension. In such cases, it would be desirable to utilize a formulation having similar characteristics to those of the prior art BDP/CFC formulations to minimize changes to existing manufacturing equipment.

Figure 6A:
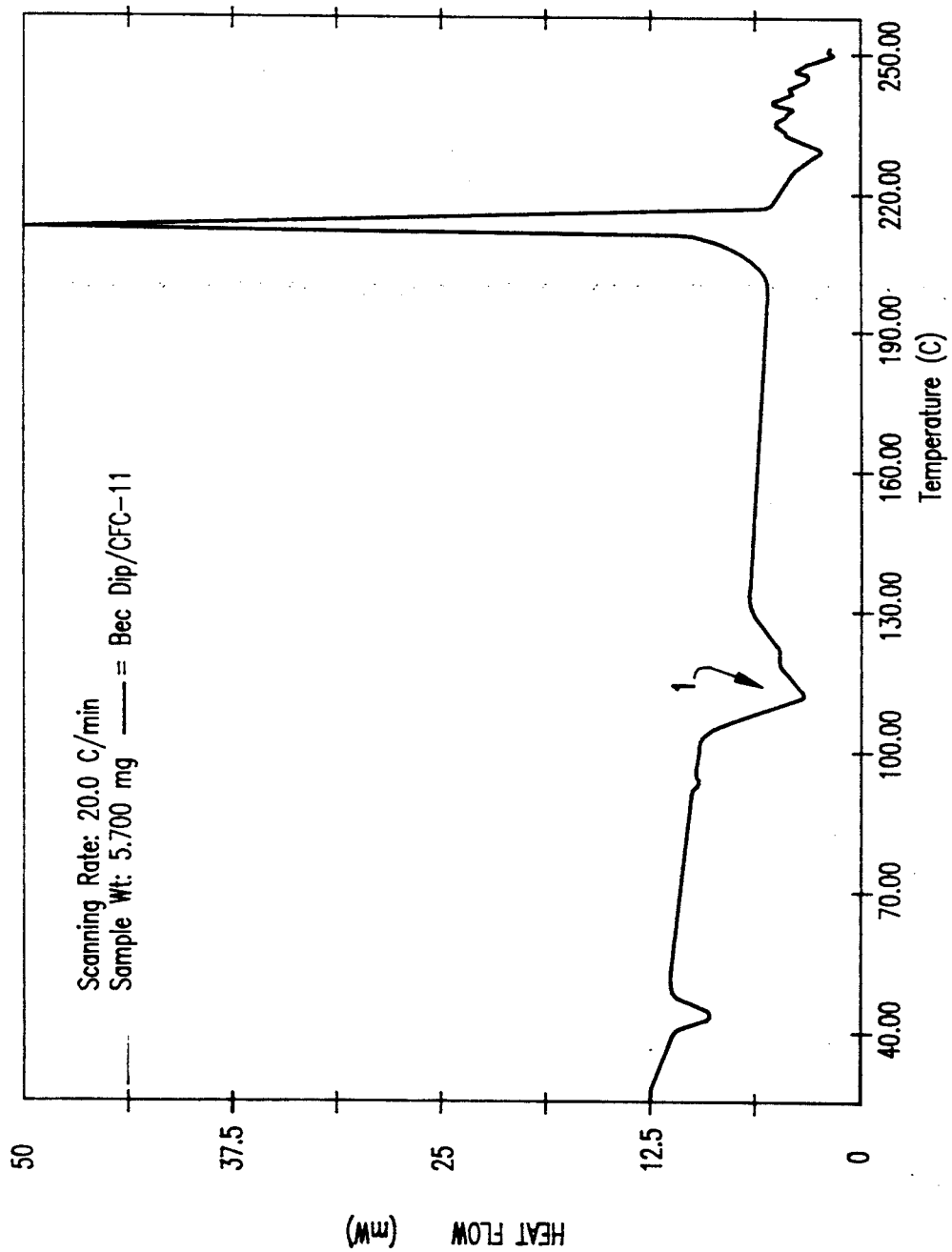
FIGS. 6a-k are differential scanning calorimetry thermograms of BDP exposed to individual propellants for 24 hours prior to propellant evaporation.
Figure 6B:
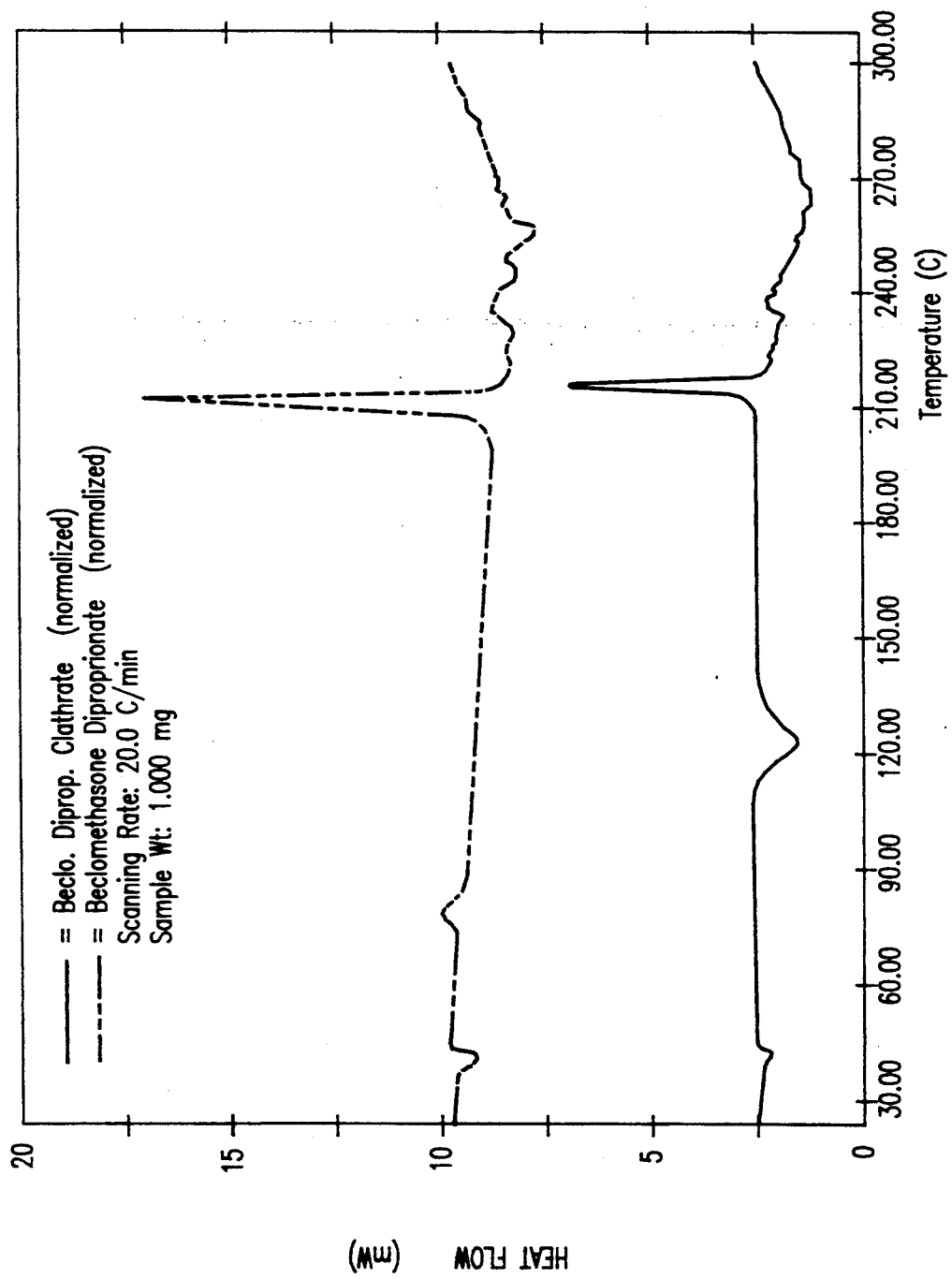
Figure 6C:
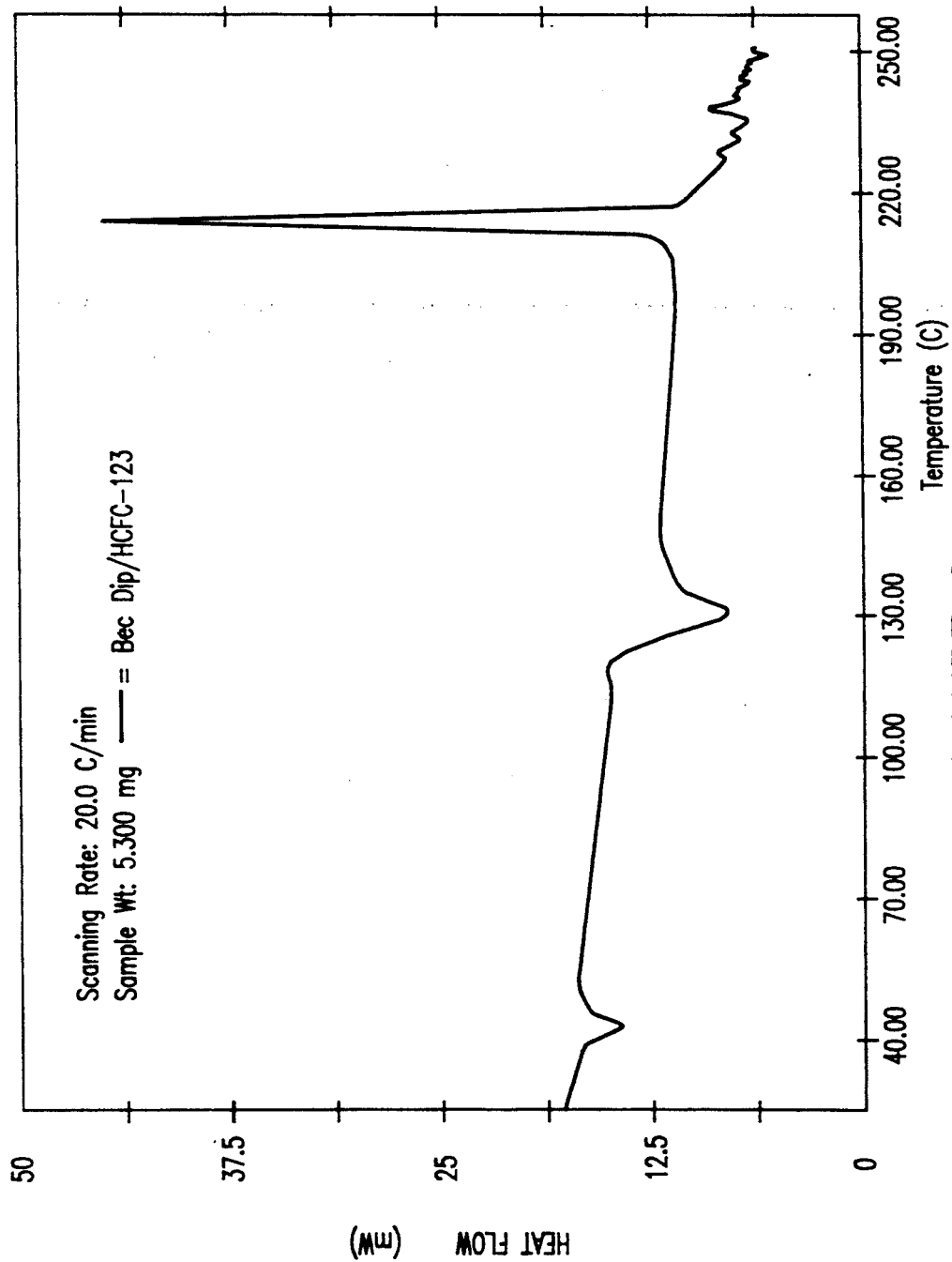
Figure 6D:
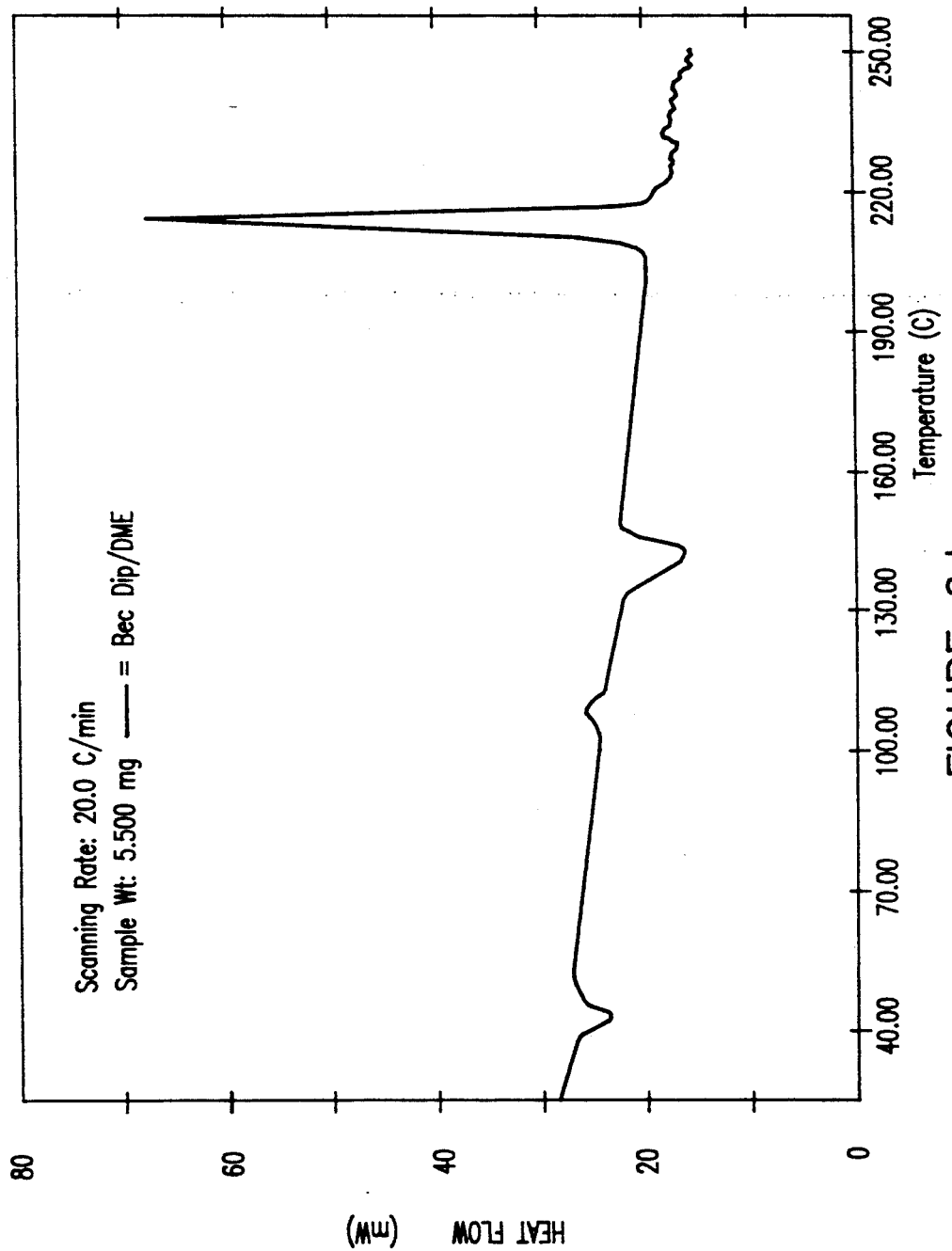
Figure 6E:
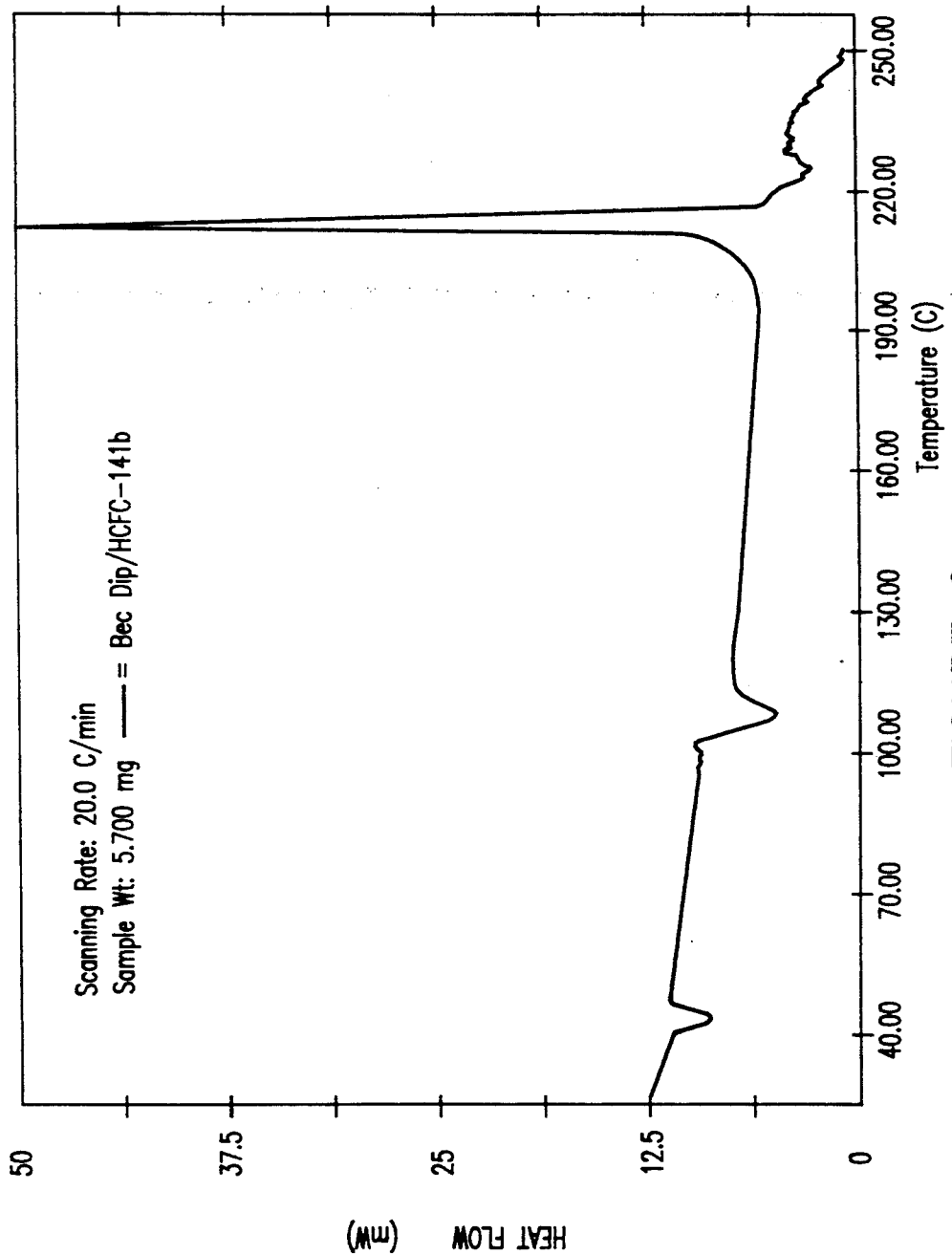
Figure 6F:
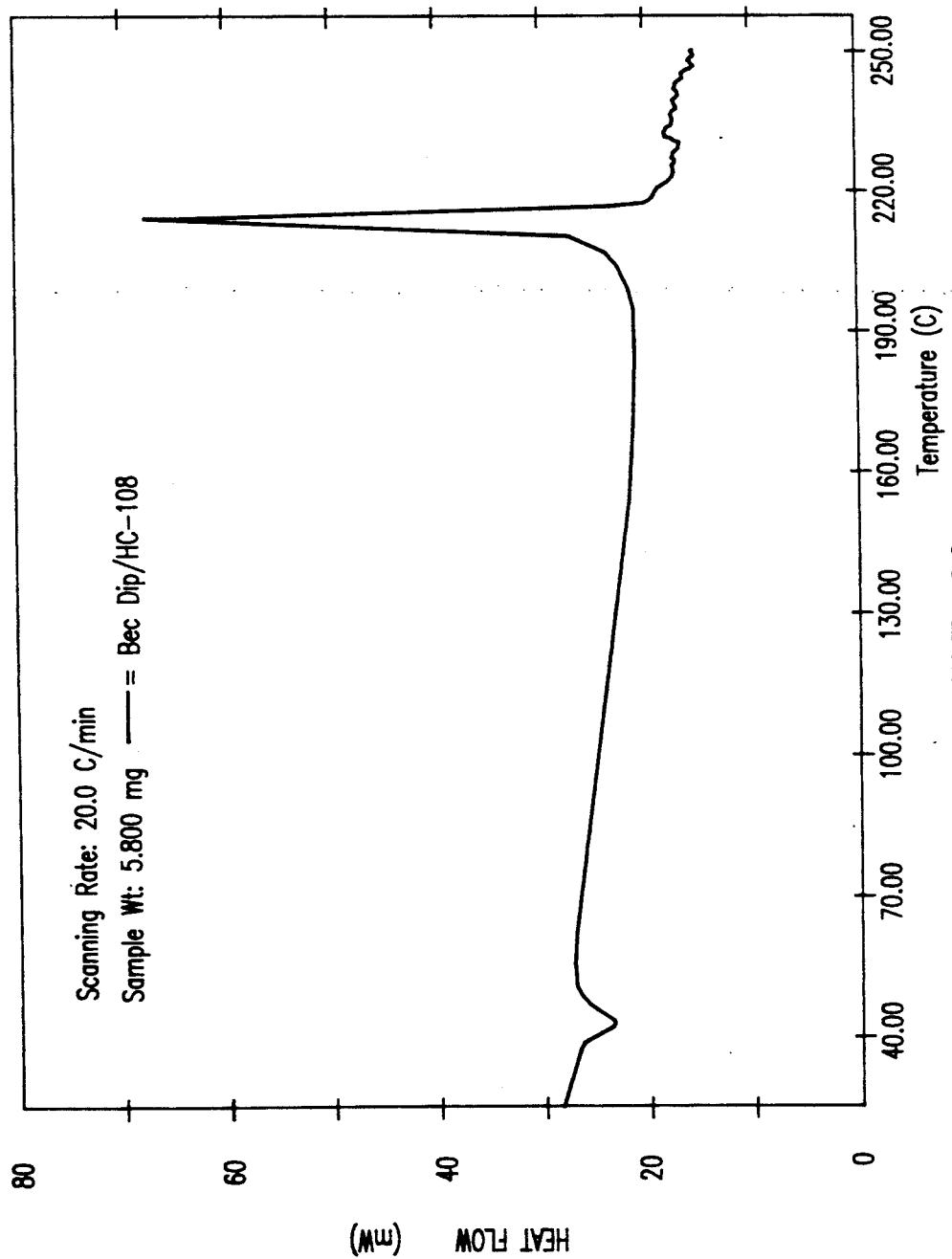
Figure 6G:
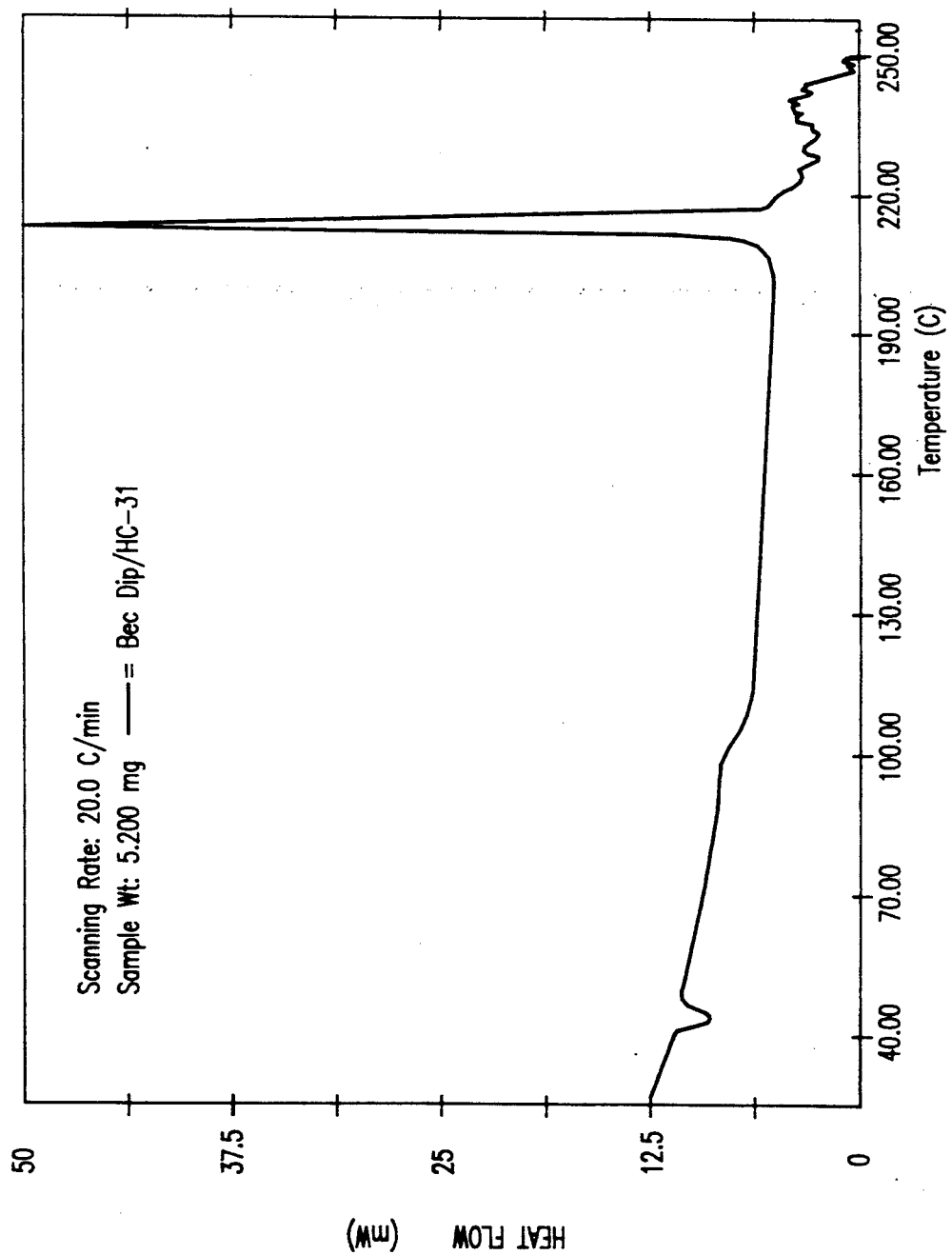
Figure 6H:
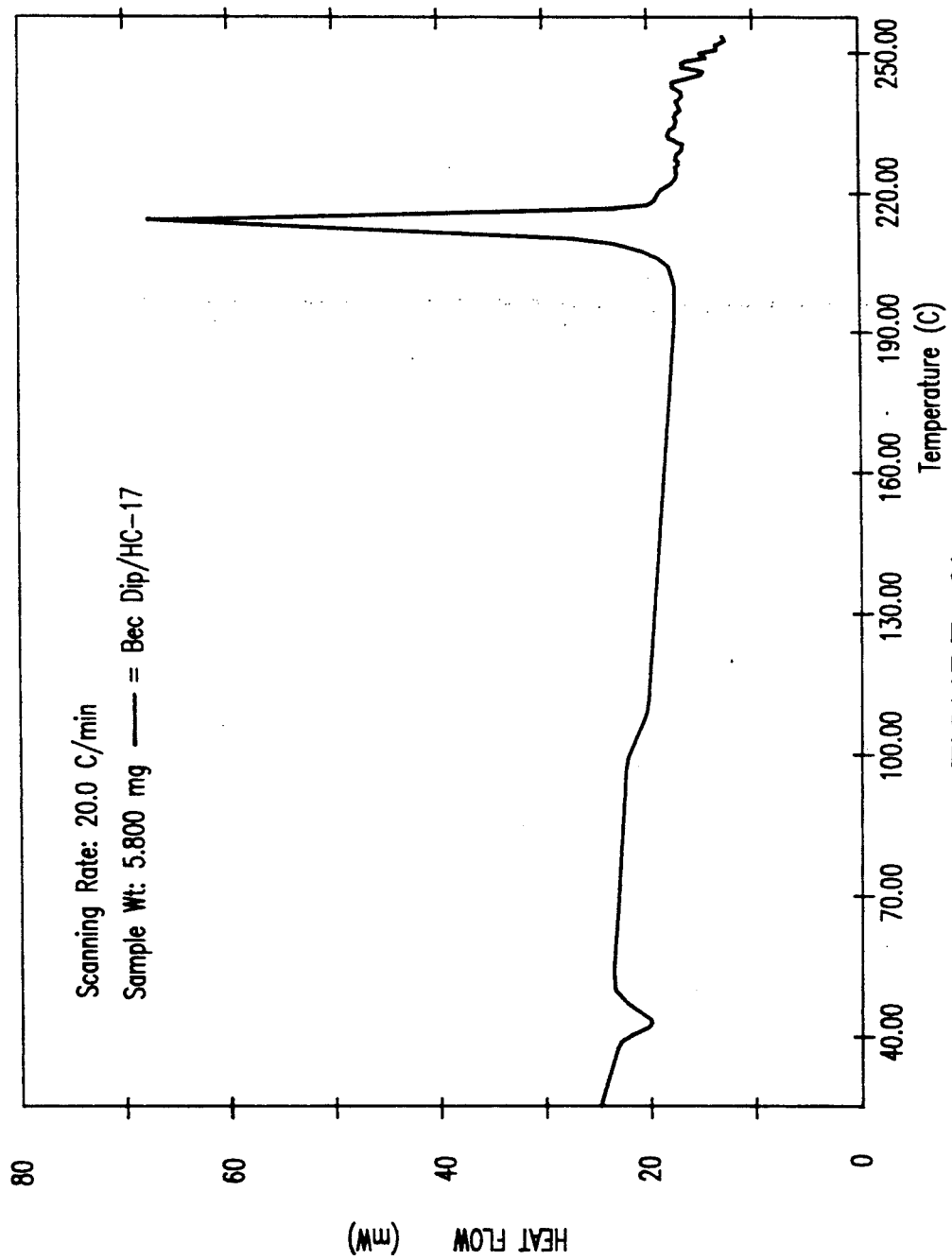
Figure 6I:
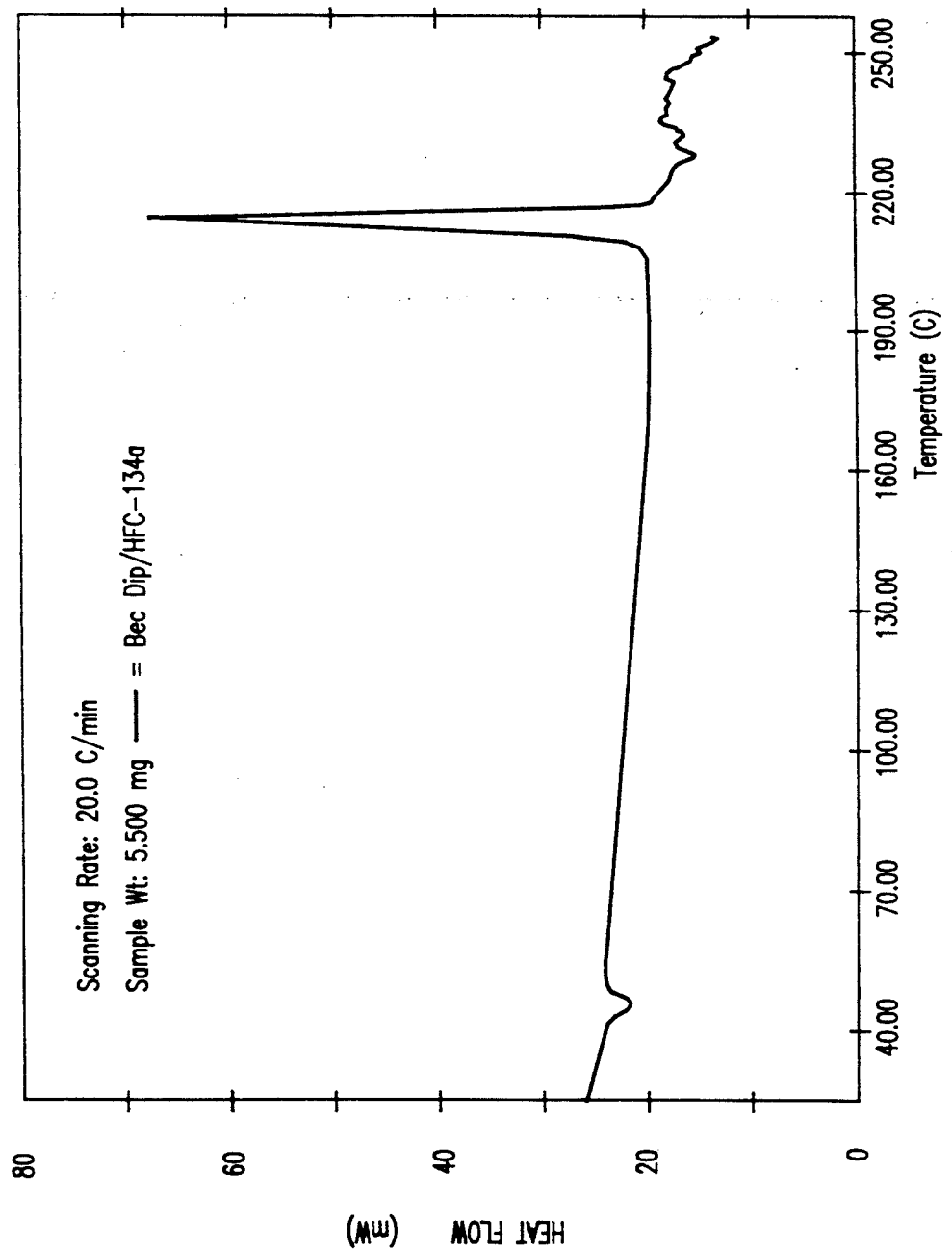
Figure 6J:
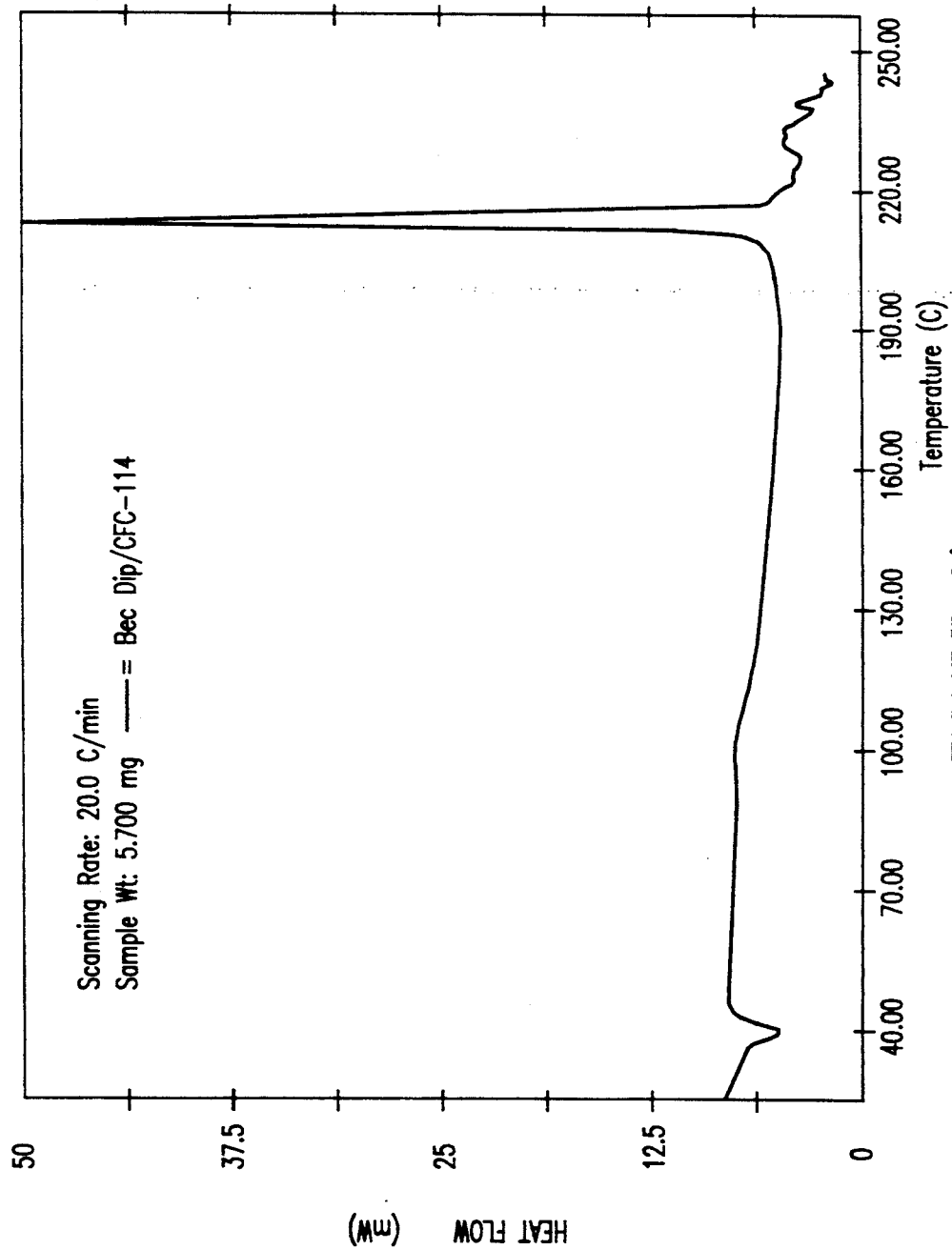
Figure 6K:
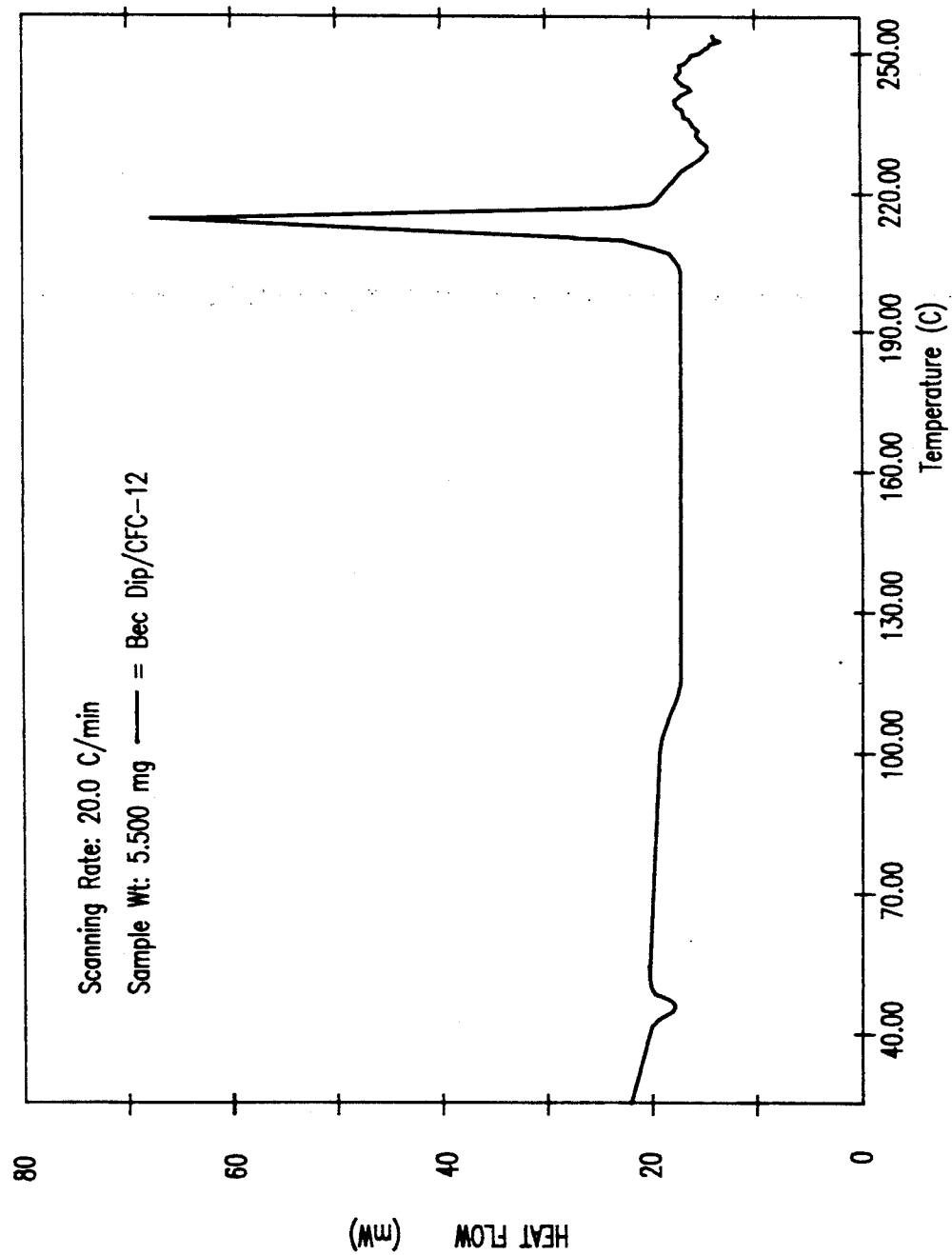

FIGS. 6a and 6c–k show DSC thermograms for BDP exposed to pure propellants. BDP was suspended in propellant for 24 hours prior to propellant evaporation. A 1–5 mg sample of the residue was crimped inside an aluminum sample pan, and heated from 25° to 250° C. at 20° C./min under a nitrogen atmosphere. A model DSC 7 from the Perkin Elmer Company of Connecticut was used. FIG. 6a is the thermogram for BDP exposed to CFC-11. Peak 1, an exothermic peak, occurs at a temperature of about 120° C. Peak 1 is attributed to the association between BDP and CFC-11, or "clathrate" formation. FIG. 6b provides a comparison of the thermograms for the BDP clathrate and untreated BDP (BDP not exposed to CFC-11). No peak is present for untreated BDP. FIGS. 6c–e show the thermograms for BDP treated with HCFC-123, DME and HCFC-141b, respectively. All three figures show exothermic peaks between 115°–140° C., indicating that there is a molecular association between BDP and these propellants (e.g., a clathrate is formed similar to the BDP and CFC-11 clathrate molecular association). This is an important finding because the data indicates that the processing technology developed for use with CFC-11 should be directly applicable to MDIs reformulated with HCFC-123, DME and HCFC-141b. The clathrates should be remicronized to a size of less than 100 μm in diameter and, more preferably, less than 10 μm in diameter, and then resuspended or dissolved in the MDI propellant. FIGS. 6f–k show the thermograms for BDP treated with other alternative propellants; specifically, HC-108, HC-31, HC-17, HFC-134a, CFC-114, and CFC-12. These propellants do not exhibit an exothermic peak and, therefore, do not form a clathrate with BDP.

Yet another consideration in the selection of alternative propellant formulations is the safety of both the manufacturer and end user. While MDIs typically contain only 10 ml of liquified propellant, it is possible that the user may smoke, thereby providing a possible source of ignition immediately after using an inhaler, or use an inhaler in other situations in which the possibility of ignition exists. In addition, production facilities that were designed to package MDIs filled with CFC-based propellant systems will not be suitable for packaging flammable propellants.

FIGS. 7a–b are tables showing the results of a flame extension test for the various MDI formulations. During testing, each MDI was fired horizontally from a distance of 10 cm into the tip of a 2 cm long propane flame using an oral inhalation actuator with an orifice diameter of 0.4 mm. The distance that the flame projected beyond the continuously burning propane flame was visually determined against a linear scale mounted behind the apparatus. The experiment was performed inside a flameproof extraction hood with the fan switched off to avoid altering the flume characteristics. The test clearly revealed that some propellant formulations containing a flammable component sprayed from metering valves will ignite if an ignition source is present. Propellant blends containing DME tended to yield the longest flame, although this should not be considered to preclude their use in MDI formulations as evidenced by the common use of flammable propellants in the hairspray and breath freshener industries. However, propellant blends containing HCFC-141b, which is widely quoted to be flammable with flammability limits in air of 7.6 to 17.7% v/v, and other non-flammable propellants such as HFC-134a were not ignitable when sprayed directly into an open flame.

FIG. 8 is a table showing the mean weight loss per actuation initially and three months after filling each unit with a test formulation. Following priming (test firing to fill the metering chamber with propellant), each MDI was weighed before and after ten actuations and the average weight loss per actuation was determined. The expected shot weight for those units which were fitted with a 63 μl metering valve was determined by multiplying the measured blend density (from FIG. 3) of the test formulation by 63/1,000. In most of the formulations, the observed shot weight was close to the expected value based on measured propellant density and valve metering volume. Moreover, the initial shot weight in many of the formulations did not alter appreciably over the three month storage period. This data demonstrates the reproducibility of valve metering for the formulations.

While the invention has been described in terms of its preferred embodiments those skilled in the art will recognize that the formulations can be varied within the spirit and scope of the appended claims.

Having thus described our invention, what we claim as new and desire to secure by Letters Patent is as follows:

1. An aerosol formulation for use in a metered dose inhaler, comprising:
    a pharmaceutically acceptable inhalable propellant; and
    a clathrate or molecular association of beclomethasone diproprionate employed as inhalable medicant dissolved or dispersed in said propellant, said clathrate or molecular association of beclomethasone diproprionate being formed with a compound selected from the group consisting of 1,1-dichloro-2,2,2-trifluoroethane, 1,1-dichloro-1-fluoroethane, and dimethyl ether, said clathrate or molecular association being of a particle size which permits inhalation.

2. An aerosol formulation as recited in claim 1 wherein said clathrate or molecular association has a particle diameter of less than 10 micrometers.

3. A clathrate or molecular association comprising of beclomethasone diproprionate and a compound selected from the group consisting of 1,1-dichloro-2,2,2-trifluoroethane, 1,1-dichloro-1-fluoroethane, and dimethyl ether, said clathrate or molecular association being of a particle size which permits inhalation.

4. An aerosol formulation for use in a metered dose inhaler, comprising:
    beclomethasone diproprionate at a concentration of 50 μg/63 μl or less; and
    a propellant combination including dimethyl ether and a propellant selected from the group consisting of isobutane, n-butane, 1,1-dichloro-2,2,2-trifluoroethane, and 1,1-dichloro-1-fluoroethane, said beclomethasone diproprionate being completely dissolved in said propellant combination.

5. The aerosol formulation of claim 4 wherein said propellant combination includes dimethyl ether and 1,1-dichloro-1-fluoroethane.

6. The aerosol formulation of claim 4 wherein said beclomethasone diproprionate is present as a clathrate or molecular association formed with a compound selected from the group consisting of 1,1-dichloro-2,2,2-trifluoroethane, 1,1-dichloro-1-fluoroethane, and dimethyl ether.

7. The aerosol formulation of claim 6 wherein said compound in said clathrate or molecular association is 1,1-dichloro-2,2,2-trifluoroethane.

8. The aerosol formulation of claim 6 wherein said compound in said clathrate or molecular association is 1,1-dichloro-1fluoroethane.

9. The aerosol formulation of claim 6 wherein said compound in said clathrate or molecular association is dimethyl ether.

10. The aerosol formulation of claim 4 wherein said dimethyl ether is present at a concentration greater than 50% of said propellant blend.

11. An aerosol formulation for use in a metered dose inhaler, comprising:
    beclomethasone diproprionate at a concentration of 50 μg/63 μl or less; and
    a propellant blend including 1,1-dichloro-2,2,2-trifluoroethane and a propellant selected from the group consisting of dimethyl ether, propane, and 1,1,1,2-tetrafluoroethane, said beclomethasone diproprionate being completely dissolved in said propellant blend.

12. The aerosol formulation of claim 11 wherein said beclomethasone diproprionate is present as a clathrate or molecular association formed with a compound selected from the group consisting of 1,1-dichloro-2,2,2-trifluoroethane, 1,1-dichloro-1-fluoroethane, and dimethyl ether.

13. The aerosol formulation of claim 12 wherein said compound in said clathrate or molecular association is 1,1-dichloro-2,2,2-trifluoroethane.

14. The aerosol formulation of claim 12 wherein said compound in said clathrate or molecular association is 1,1-dichloro-1-fluoroethane.

15. The aerosol formulation of claim 12 wherein said compound in said clathrate or molecular association is dimethyl ether.

16. The aerosol formulation of claim 1 wherein said compound in said clathrate or molecular association is 1,1-dichloro-2,2,2-trifluoroethane.

17. The aerosol formulation of claim 1 wherein said compound in said clathrate or molecular association is 1,1-dichloro-1-fluoroethane.

18. The aerosol formulation of claim 1 wherein said pharmaceutically acceptable inhalable propellent is selected from the group consisting of trichlorofluoromethane, dichlorofluoromethane, 1,2-dichloro-1,1,2,2-tetrafluoroethane, 1,1-dichloro-1-fluoroethane, 1,1-dichloro-2,2,2-trifluoroethane, 1,1,1,2-tetrafluoroethane, n-butane, isobutane, propane, perfluoropentane, and dimethyl ether.

19. The clathrate or molecular association of claim 3 wherein said compound is dimethyl ether.

20. The clathrate or molecular association of claim 3 wherein said compound is 1,1-dichloro-1-fluoroethane.

21. The clathrate or molecular association of claim 5 wherein said compound is 1,1-dichloro-2,2,2-trifluoroethane.

* * * * *